United States Patent [19]

Wheeler et al.

[11] Patent Number: 5,051,431

[45] Date of Patent: Sep. 24, 1991

[54] PYRIDONE NITRILES USEFUL IN TREATING CARDIOVASCULAR DISEASE

[75] Inventors: Thomas N. Wheeler, Raleigh; Terrence P. Kenakin, Durham; Joel E. Shaffer, Chapel Hill, all of N.C.

[73] Assignee: Glaxo Inc., Research Triangle Park, N.C.

[21] Appl. No.: 565,297

[22] Filed: Aug. 9, 1990

Related U.S. Application Data

[63] Continuation-in-part of Ser. No. 411,065, Sep. 22, 1989, abandoned.

[51] Int. Cl.$^5$ .................. C07D 213/64; A61K 31/44
[52] U.S. Cl. .................. 514/344; 514/235.5; 544/131; 546/277; 546/287; 546/288
[58] Field of Search ............... 544/131; 546/277, 287, 546/288; 514/344, 235.5

[56] References Cited

U.S. PATENT DOCUMENTS

| | | | |
|---|---|---|---|
| 4,397,854 | 8/1983 | Sicar | 544/239 |
| 4,413,127 | 11/1983 | Singh | 546/249 |
| 4,608,383 | 8/1986 | Wiedemann | 514/407 |

FOREIGN PATENT DOCUMENTS

| | | |
|---|---|---|
| 39892 | 11/1981 | European Pat. Off. |
| 178189 | 4/1986 | European Pat. Off. |
| 236624 | 9/1987 | European Pat. Off. |
| 259835 | 3/1988 | European Pat. Off. |

OTHER PUBLICATIONS

Slater, R. A. et al., J. Med. Chem. 31, pp. 345-351 (1988).

Curran, W. V. et al., J. Med. Chem., vol. 17, No. 3, pp. 273-281 (1974).

*Primary Examiner*—Mary C. Lee
*Assistant Examiner*—Lenora A. Mittenberger
*Attorney, Agent, or Firm*—David J. Levy

[57] ABSTRACT

Pyridones of formula (I) for treating congestive heart failure:

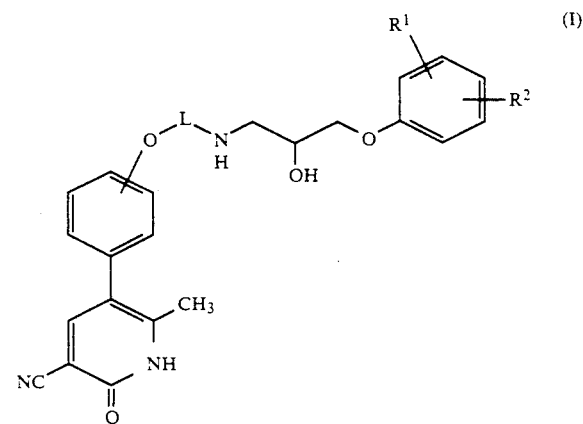

wherein:
R$^1$ and R$^2$ are a variety of phenyl substituents, L is a divalent alkylene or amide containing alkylene linking group. Pharmaceutical composition, methods for their use in treating cardiovascular conditions, processes used in synthesis and intermediates used in such processes.

13 Claims, No Drawings

PYRIDONE NITRILES USEFUL IN TREATING CARDIOVASCULAR DISEASE

This is a continuation-in-part of U.S. Ser. No. 07/411,065 filed Sept. 22, 1989, now abandoned.

BACKGROUND OF THE INVENTION

Congestive heart failure (CHF) is the disease state wherein a weakened heart results in the inability to adequately pump blood throughout the body. CHF is a common cause of death in the hospital and is an expensive and time consuming condition to treat. Positive inotropic pharmaceuticals such as amrinone act by increasing the force of contraction of the heart without increasing heart rate and have been proposed to treat CHF. Presumably these agents produce their cardiotonic effects at least partly through inhibition of type III phosphodiesterase.

Beta-blockers such as atenolol and propranolol may be given to persons who have suffered a heart attack in order to lessen oxygen consumption by the heart and prevent sudden death. However, if there is significant damage to the heart, there may be a lack of ability to pump forcefully and the negative inotropic effects of a beta-blocker may exacerbate an already dangerous situation.

Propanolamines having a heterocyclic moiety which may be pyridine are set forth in U.S. Pat. No. 4,608,383. Hydroxyalkylaminoalkyl substituted salicylamides having beta blocking or beta-stimulating activities are taught in European Patent 39,892 published Nov. 18, 1981. N-Heterocyclyl amines as beta agonists are taught in European Patent 236,624 published Sept. 16, 1987.

European Patent 178,189 published Apr. 16, 1986 teaches pyridazinones having a phenyl group at the 6-position. Pyridazinones having an alkylaminophenyl group at the 6-position are taught in European Patent 259,835 published Mar. 16, 1988.

SUMMARY OF THE INVENTION

This invention relates to novel pyridones of the following formula (I) or salts thereof as well as pharmaceutical compositions, methods for their use in treating cardiovascular conditions, processes used in syntheses and intermediates used in such processes.

DETAILED DESCRIPTION OF THE INVENTION

This invention relates to novel chemical compounds and pharmaceutical compositions thereof. The subject chemical compounds are 5-phenyl-2-pyridones of the formula (I):

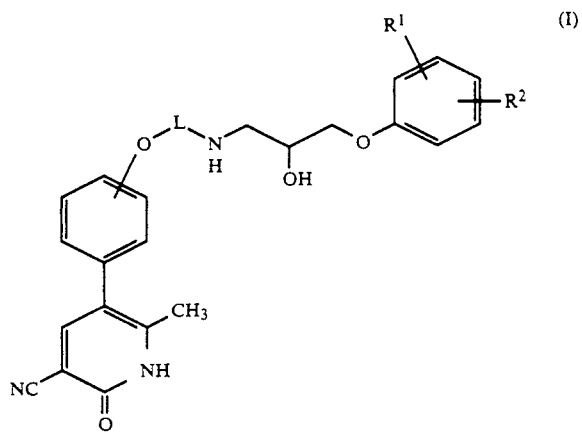

wherein:
$R^1$ and $R^2$ represent, independently, hydrogen, alkyloxy, morpholino, cyano, halogen, trifluoromethyl, alkyl, alkylsulfonyl, alkyloxyalkyl, cycloalkylalkyloxyalkyl, nitro, hydroxy, alkenyloxy, amino or amino substituted by one or two alkyl groups;

L represents a linking moiety of the following formula (II) or (III):

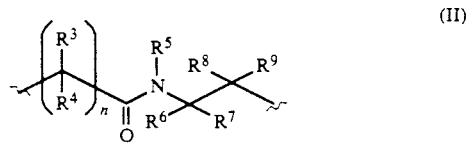

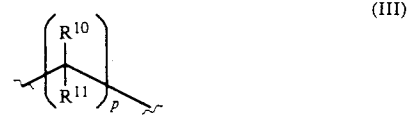

in which:
$R^3$-$R^{11}$ represent, independently, hydrogen or lower alkyl;
n represents the integer 1,2 or 3;
p represents the integer 2,3,4,5 or 6; or a pharmaceutically acceptable acid addition salt thereof.

As used herein, "lower alkyl" per se or as part of another group such as lower alkoxy may be 1 to 3 carbons, straight or branched chain; "alkyl" may be of about 1 to 6 carbons, straight or branched chain; "cycloalkyl" may be 3 to 7 carbons; "independently" indicates that members, where two or more are present, need not be identical as in the definitions of $R^1$ and $R^2$ or the various possibilities for $R^3$ when n is 2 or 3; "halogen" is fluoro, chloro, bromo, or iodo; the L group is attached as shown in the definition i.e. the carbon, carrying $R^3$ and $R^4$ in formula (II) is attached to the left most oxygen of —OLNH— of formula (I) rather than the nitrogen; the wavy lines in formulae (II) and (III) indicated the bond of attachment of L; and morpholino may be attached via the nitrogen or any ring carbon. Placement of the —O—L— moiety on the phenyl ring in formula (I) which is attached to the 5-position of the pyridone may be at any of the 2-, 3- or 4-positions.

Particular compounds of this invention are those of formula (I) with one or more of the following definitions: L is the linking group of formula (II); n is 1 or 3;

$R^3$, $R^4$, $R^5$, $R^6$, $R^7$, $R^{10}$ and $R^{11}$ are hydrogen; $R^8$ and $R^9$ are methyl groups; $R^1$ is hydrogen, and $R^2$ is a cyano, chlorine, or methyl substituted at position 2 of the phenyl ring. The —O—L— moiety is particularly at the 4-position of phenyl ring which is, in turn, attached to the 5-position of the pyridone ring.

The compounds of formula (I) contain a basic nitrogen atom and hence can form pharmaceutically acceptable acid addition salts. A wide variety of acids may be employed to form such salts and representative examples of such acids include inorganic acids, e.g. hydrochloric acid, hydrobromic acid, hydroiodic acid, phosphoric acid, nitric acid, and sulfuric acid; and organic acids, e.g. maleic acid, fumaric acid, acetic acid, benozoic acid, p-toluenesulfonic acid, tartaric acid, citric acid, succinic acid, lactic acid, and propionic acid. These acid addition salts are prepared by conventions methods. Compounds of the formula (I) may also exist as a solvate, e.g. a hydrate or hemihydrate, and such are within the scope of the invention.

The compounds of formula (I) have one or more asymmetric carbon atoms in their structure and consequently they may exist in different optical isomeric forms or mixtures, e.g. racemates or mixtures of diastereomers. Enantiomeric forms and mixtures of such forms may be obtained separate by application of methods of resolution known to those skilled in the art such as, for example, salt formation with an optically active acid followed by selective crystallization or chiral derivatization followed by selective crystallization or silica gel chromatography. All stereoisomeric forms of the compounds of formula (I) including mixtures of diastereomers, pure diastereomers enantiomers, and mixtures thereof are understood to be within the scope of this invention.

PROCESSES

The compounds of formula (I) in which the linking moiety L is of the formula (II) may be prepared as shown in Scheme I.

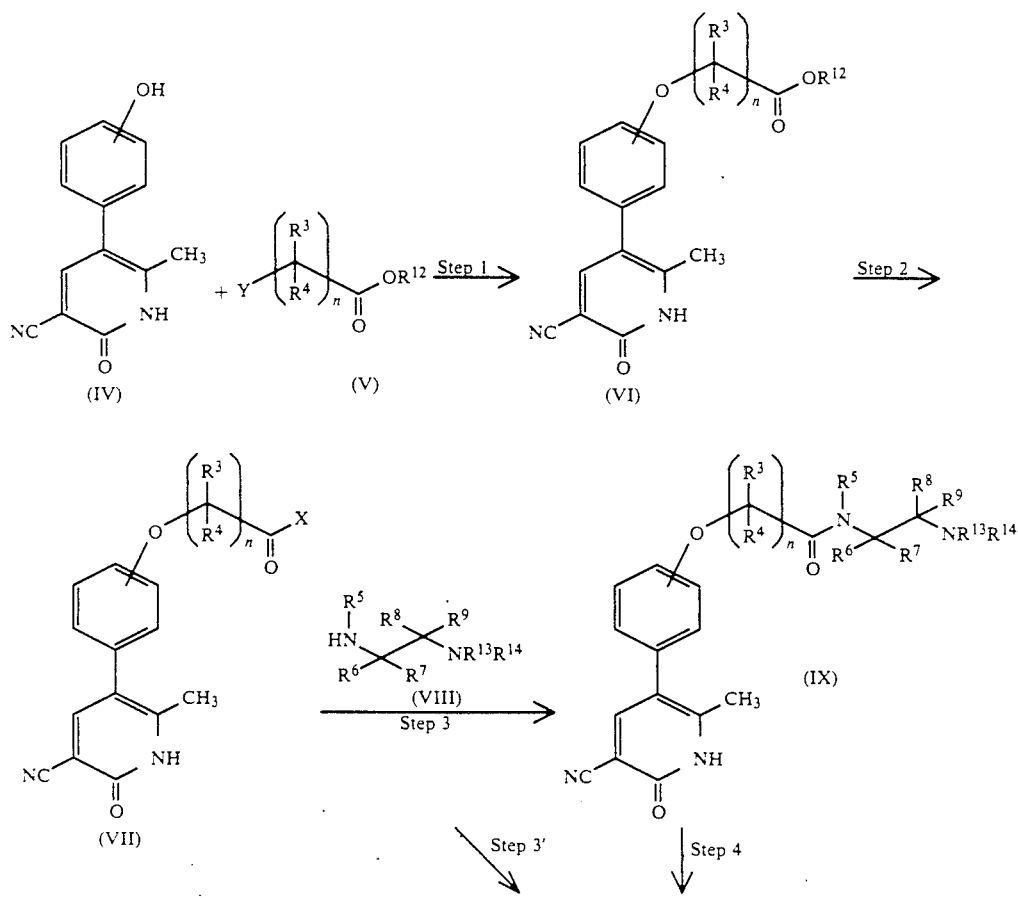

Scheme I

-continued
Scheme I

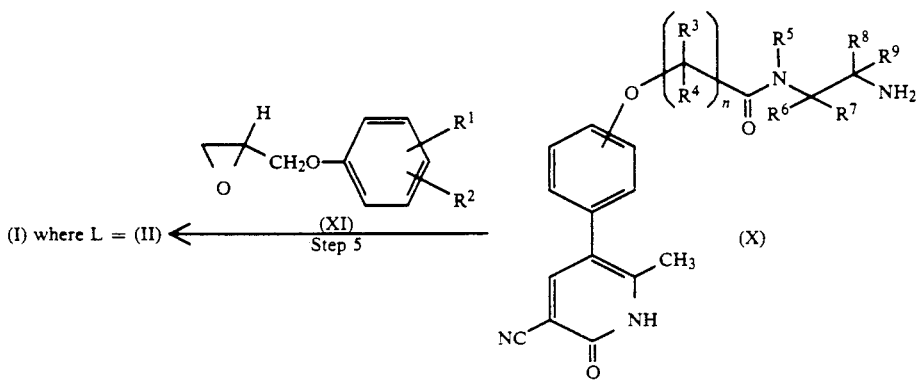

In Scheme I, the various R groups, except $R^{12}$, and $R^{14}$, and n are as defined for formula (I).

The compounds of formula (IV) employed as starting materials in Scheme I may be prepared by the methods described by G. Y. Lesher et al, U.S. Pat. No. 4,465,686. In the compounds of formula (V), Y represents a leaving group that is reactive toward displacement by nucleophiles. Suitable Y groups include halogen or the p-toluenesulfonate ester, p-nitrobenzenesulfonate ester, methansulfonate ester and trifluoromethanesulfonate ester. $R^{12}$ in formula (V) represents a lower alkyl group. The compounds of formula (V) are known compounds or may be prepared from known compounds by conventional methods.

Step 1 of Scheme I is effected by reacting the phenol of formula (IV) with a compound of formula (V) in the presence of a suitable base and appropriate solvent to give compounds of formula (VI). Bases which may be used include sodium hydride, sodium t-butoxide, and similar non-nucleophilic basic reagents. The preferred base is sodium hydride.

A wide variety of solvents may be used in Step 1 of Scheme I with the only restriction being that the solvent be inert toward starting materials (IV) and (V) as well as to the basic reagent and the product (VI). Suitable solvents include DMF, dimethylsulfoxide, aromatic hydrocarbons such as benzene or toluene, and ethers such as tetrahydrofuran. Step may be conducted over a wide temperature range, with the preferred temperature being about 0° C. to 80° C. The preferred conditions for effecting Step 1 of Scheme I is to use sodium hydride as the base, dimethylformamide as the solvent, and a temperature of 0° C. with gradual warming to 80° C. Under these conditions, Step 1 is completed in 2-4 hr.

Step 2 of Scheme I is effected by heating the ester of formula (VI) in an aqueous solution containing a suitable base. Suitable bases which may be used include sodium hydroxide, potassium hydroxide, potassium carbonate, and the like. Suitable co-solvents with water for use in Step 2 include alcohols, e.g. methanol, ethanol, and propanol ethers, e.g. tetrahydrofuran and dioxane, and dimethylsulfoxide. Step 2 may be conducted over a wide temperature range, with the preferred conditions for effecting Step 2 of Scheme I being to use potassium hydroxide as the base, 1:1 water-ethanol as the solvent, and a temperature of 80° C. Under these conditions, Step 2 is completed in 2-4 hr.

In the compound of formula (VII), X is a leaving group such as hydroxy whereby (VII) is a carboxylic acid. Alternatively, the compound of formula (VII) where X is hydroxy may be converted to a suitable reactive derivative which is then reacted with an amine of formula (V). Suitable reactive derivatives of the carboxylic acid (VII) include: acid halides, such as the acid chloride; mixed anhydrides of the carboxylic acid with another organic acid, such as acetic acid, propionic acid, or pivalic acid whereby X is —OCOR where R is an organic moiety such as alkyl; acyl imidazoles; and active esters of carboxylic acid, such as the 4-nitrophenyl ester. With the exception of the acyl imidazole, these reactive derivatives can be prepared by treating the carboxylic acid with a suitable halogen compound, such as thionyl or oxalyl chloride, acetyl chloride, pivaloyl chloride, or isobutoxycarbonyl chloride in the presence of a proton acceptor and an inert solvent. Suitable proton acceptors include both organic bases such as triethylamine or 4-dimethylaminopyridine and inorganic bases such as anhydrous potassium carbonate. Suitable solvents for forming reactive derivatives of (VII) where X=OH include diethyl ether, tetrahydrofuran, aromatic hydrocarbon solvents such as benzene or toluene, methylene chloride, and acetonitrile. Acyl imidazoles can be prepared from (VII) where X=OH by reaction of (VII) with 1,1'-carbonyldiimidazole. Thus, X in formula (VII) may specifically be hydroxy, chloro, acetoxy, propionoxy, pivaloxy, isobutoxycarbonyloxy or an imidazole group.

In the compounds of formula (VIII) and (IX) in Scheme I, $R^{13}$ represents hydrogen and $R^{14}$ represents any of several monovalent amine protecting groups including, but not limited to carbamates, e.g. —$CO_2C(CH_3)_3$ or —$CO_2CH_2CH_3$, or N-benzyl derivatives, e.g. benzyl, or $R^{13}$ and $R^{14}$ together represent a divalent amine protecting group such as phthalimide, e.g. by reaction of the free amine with phthallic anhydride. Detailed examples of the use and removal of these amine protecting groups are described by T. W. Greene in Protective Groups in Organic Synthesis, John Wiley & Sons, 1981, pp. 218-323.

Depending upon the definition of $R^6$, $R^7$, $R^8$ and $R^9$, an amine protecting group $R^{14}$ or $R^{13}$ and $R^{14}$ may not be necessary. In those cases, Step 4 of Scheme I, removal of the amine protecting group is unnecessary and the intermediate (X) is prepared directly from (VII) via Step 3' with a diamine of the formula $HR^5NC(R^6R^7)C(R^8R^9)NH_2$.

The amines of formula (VIII) are commercially available or may be prepared by conventional methods, for example, see the *Journal of Medicinal Chemistry*, 31, 898–901 (1988).

Steps 3 and 3' in Scheme I are coupling reactions and may be executed by treating a mixture of compounds (VII) and (VIII) in the presence of inert solvent with suitable dehydrating agents such as diethylcyanophosphonate or dicyclohexylcarbodiimide. The reaction may be carried out over a wide range of temperatures, with the preferred temperature being 0° C. to 75° C. Suitable solvents for the coupling reaction are tetrahydrofuran, acetonitrile, benzene, toluene, methylene chloride, chloroform, and DMF. The preferred conditions for effecting steps 3 or 3' is to use diethylcyanophosphonate as the coupling agent, dimethyformamide as the solvent, and a temperature of 0° C. to 25° C. Under these conditions the time required for reaction is about 1–12 hr.

Step 4 of Scheme I, removal of the amine protective group $R^{14}$ or $R^{13}$ and $R^{14}$, is executed under conditions appropriate to the particular amine protective group. A preferred amine protective group is the tert-butoxycarbonyl group. When $R^{14}$ in Scheme I represents the tert-butoxycarbonyl group, Step 4 is effected by treating the compound of formula (IX) with an acid solution which may be either a mineral acid such as hydrochloric acid, hydrobromic acid, or sulfuric acid or an organic acid such as p-toluenesulfonic acid or trifluoroacetic acid. A wide range of solvents may be used for removal of the tert-butoxycarbonyl group as long as the solvent is stable to acids and does not react with the amine product, (X). Suitable solvents include the halogenated hydrocarbons, such as methylene chloride and chloroform, and aromatic solvents such as benzene and toluene. The reaction may be run over a wide range of temperatures, in particular in the temperature range of 0° C. to 25° C. The time required for the reaction is about 15 min to 2 hr and depends upon the solvent and temperature of the reaction. Removal of other amine protecting groups may be as set forth in the description below of Step 2 of Scheme IV.

Step 5 in Scheme I is effected by reacting an amine of formula (X) with an epoxide of formula (XI). Epoxides of the formula (XI) are either known compounds or can be prepared by conventional procedures well known to those skilled in the art of organic synthesis. Particular compounds of formula (I) are the enantiomers wherein the carbon bearing the hydroxyl group has the S-configuration. It may be thus of particular utility to utilize in Step 5 epoxides of the formula (XI) having the S-configuration at the asymmetric carbon, since these epoxides will yield structures having the S-configuration at the carbon bearing the hydroxyl group. Many of the examples of compounds of formula (I) prepared and tested have been mixtures of the 2S- and 2R-hydroxy configurations and thus the invention covers all such stereoisomers. The desired S-epoxides are prepared as shown in Scheme II using the procedures described by K. B. Sharpless, J. M. Klunder and T. Onami in the *Journal of Organic Chemistry*, 1989, 54, 1295–1304.

Scheme II

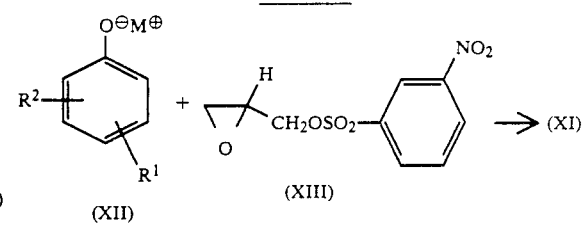

In Scheme II, $R^1$ and $R^2$ are as defined above for formula (I). In Scheme II, a phenolic salt of the formula (XII) is reacted with a sulfonate of formula (XIII) at 0° C. to 75° C. to yield the epoxide (XI). The (2S)-(±)-glycidyl 3-nitrobenzenesulfonate form of the compound of formula (XIII) shown in Scheme II is commercially available from the Aldrich Chemical Company or may be prepared by the methods cited in the Sharpless et al reference given above. Suitable salts for the reaction shown in Scheme II include the sodium and potassium salts, i.e. $M^+ = Na^+$ or $K^+$. The phenolic salts (XII) are prepared from the corresponding phenols which are known compounds that are commercially available or can be prepared by conventional methods.

A wide variety of solvents may be employed in Step 5 of Scheme I, with the only restriction being that the solvent must be inert with respect to the amines (X), epoxides (XI), and products (I). Suitable solvents for Step 5 include alcohols such as methanol, ethanol, or isopropanol; aromatic hydrocarbon solvents such as benzene or toluene, and ethers such as tetrahydrofuran or dioxane. The reaction in Step 5 may be run over a wide range of temperatures, in particular in the range of 25° C. to 100° C. The time required for the reaction of Step 5 is dependent upon temperature and the nature of the substituents $R^8$ and $R^9$; however, a time span of 3–24 hr is usually sufficient for completion of the reaction.

An alternative method that has been employed in certain instances to prepare compounds of formula (I) in which the L group is (II) is shown in Scheme III:

Scheme III

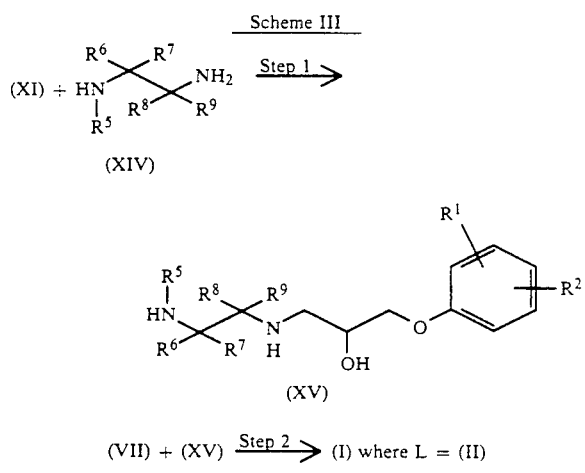

(VII) + (XV) $\xrightarrow{\text{Step 2}}$ (I) where L = (II)

In Scheme III all R groups are as previously defined. Step 1 in Scheme III is executed as previously described for Step 5 of Scheme I and Step 2 of Scheme III is effected as described for Step 3 of Scheme I. Thus, the epoxide (XI) is reacted with the diamine (XIV), or a protected derivative as explained below, to yield the intermediate (XV) which is then condensed with the pyridinecarbonitrile (VII) to yield the product of the invention (I) where L is moiety (II).

The method shown in Scheme III for the preparation of compounds of formula (I) with L=(II) is most advantageously employed when $R^5$-$R^9$ are all hydrogen or when $R^6=R^7=CH_3$ and $R^8=R^9=H$. A protected form of the ethylenediamine compound of formula (XIV), e.g. 2-(tert-butoxycarbamoyl)ethylamine, may be used to avoid formation of the bis derivative although simply using an excess of the formula (XIV) amine will usually insure that only the 1:1 adduct is formed. Thus, the amine-protected form of the amine of formula (XIV) having an amine protecting group in the place of the hydrogen on the nitrogen bearing $R^5$ is reacted in Step 1 of Scheme III and the product, bearing the protecting group on the nitrogen bearing $R^5$, is deprotected by conventional means to yield the product of formula (XV).

The compounds of formula (I) in which L is a group of the formula (III) may be prepared as shown in Scheme IV:

sponding halo- or hydroxyalkylamines by conventional methods well known to those skilled in the art.

Step 1 in Scheme IV is effected by reacting the phenol of formula (IV) with a compound of the formula (XVI) in the presence of a suitable base and appropriate solvent to give compounds of formula (XVII). Bases which may be used in Step 1 include sodium hydride, sodium t-butoxide, and similar non-nucleophilic basic reagents. The preferred base is sodium hydride.

A wide variety of solvents may be used in Step 1 of Scheme IV with the only restriction being that the solvent be inert toward starting materials (IV) and (XVI) as well as to the basic reagent and the product (XVII). Suitable solvents include DMF, dimethylsulfoxide, aromatic hydrocarbons such as benzene or toluene, and ethers such as tetrahydrofuran. Step 1 may be conducted over a wide temperature range, with the preferred temperature being 25° C. to 100° C. The preferred conditions for effecting Step 1 of Scheme IV is to use sodium hydride (2.0 equivalents) as the base, dimethylformamide as the solvent, and a temperature of

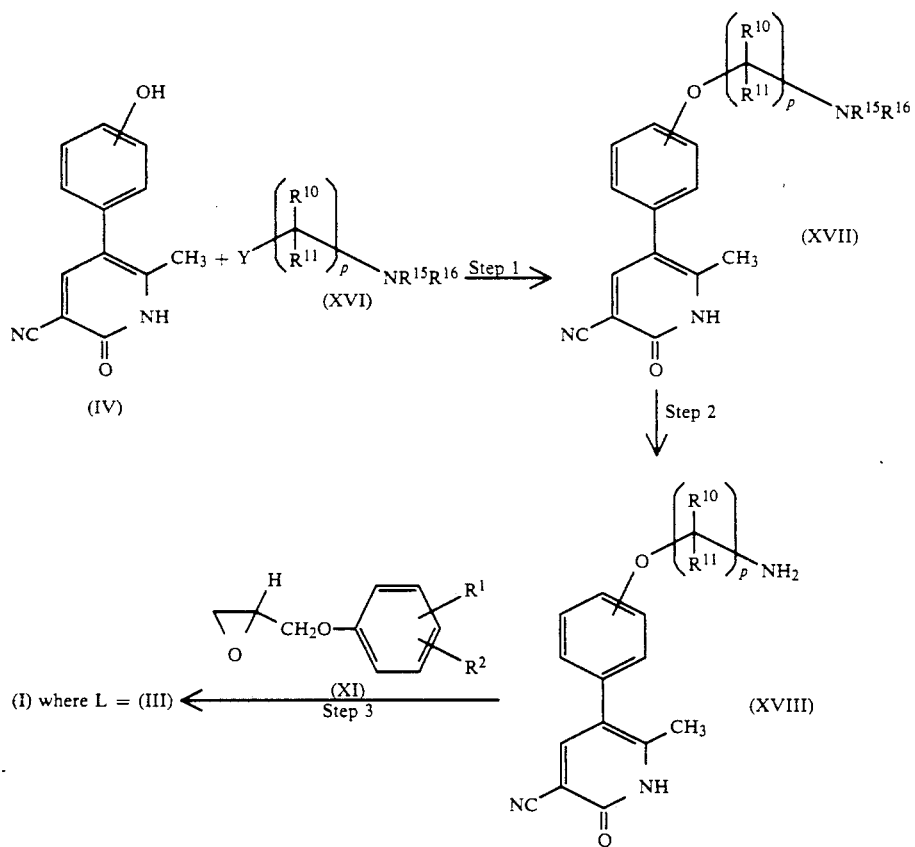

Scheme IV

The compounds of formula (XVI) represent protected alkylamines with a leaving group, Y, at one end of the chain that is reactive toward displacement by nucleophiles. Suitable Y groups include halogen and p-toluenesulfonate and p-nitrobenzenesulfonate esters. In Scheme IV, and $R^{15}$ and $R^{16}$ are as defined in Scheme I for $R^{13}$ and $R^{14}$. Suitable amine protecting groups $R^{15}$ and $R^{16}$ include, together with the nitrogen to which they are attached, a phthalimide group, carbamates, and N-benzylated amines. The compounds of formula (XV) are either known or may be prepared from the corre- 60° C. to 80° C. Under these conditions, Step 1 is completed in 2-6 hr.

The nature of the reaction conditions for Step 2 of Scheme IV are dependent upon the amine protecting group $R^{16}$ or $R^{15}$ and $R^{16}$ that has been employed. If the amine protective group is a carbamate moiety such as the tert-butoxycarbamoyl group, it may be removed under acid hydrolysis conditions. Reaction conditions and suitable acids are the same as those described earlier for Step 4 of Scheme I. If the protecting group is a phthalimide, it is conveniently removed by treatment of a compound of the formula (XVII) with hydrazine in a suitable solvent. Solvents that may be used for this reaction include alcohols, e.g. ethanol or isopropanol, ethers such as tetrahydrofuran, acetonitrile, or aromatic hydrocarbon solvents such as benzene or toluene. The reaction may be executed over a wide temperature range, with the preferred temperature range being about 25° C. to 100° C. If the protecting group in formula (XVII) is an N-benzylated amine, then the removal of the protection group (Step 2) in Scheme IV is conveniently accomplished by catalytic reduction. Suitable catalysts for this reaction include platinum or palladium supported on activated charcoal. The reaction is carried out under a pressure of 1-3 atmospheres of hydrogen in the temperature range of about 25° C. to 70° C.

Step 3 in Scheme IV is carried out by reacting the amine (XVIII) with an epoxide of the formula (XI) as described for Step 5 of Scheme I.

SPECIFIC COMPOUNDS

Specific examples of the compounds of the present invention are those of the formula (I) set forth in the following Table I where the "—O—L— Position" refers to position of substitution on the phenyl ring.

TABLE I

| Formula (I): $R^3, R^4, R^5, R^6, R^7, R^{10}$ & $R^{11}$ = H | | | | | | |
|---|---|---|---|---|---|---|
| Example | L | -O-L-Position | n | p | $R^8R^9$ | $R^1R^2$ |
| 1 | II | 4 | 1 | — | H,H | H,H |
| 2 | II | 4 | 3 | — | H,H | H,H |
| 3 | III | 4 | — | 3 | — | H,H |
| 4 | II | 3 | 1 | — | H,H | H,H |
| 5 | II | 3 | 3 | — | H,H | H,H |
| 6 | II | 2 | 1 | — | H,H | H,H |
| 7 | II | 2 | 3 | — | H,H | H,H |
| 8 | II | 4 | 3 | — | $CH_3,CH_3$ | H,2-CN |
| 9 | III | 4 | — | 3 | — | H,2-CN |
| 10 | II | 4 | 3 | — | $CH_3,CH_3$ | H,2-Cl |
| 11 | II | 4 | 1 | — | $CH_3,CH_3$ | H,2-CN |
| 12 | II | 4 | 1 | — | $CH_3,CH_3$ | H,2-Cl |
| 13 | II | 4 | 1 | — | $CH_3,CH_3$ | 2-CN, 5-Cl |

Also part of the present invention are intermediates used in the various processes of the invention including those of formulae (VI), (VII), (X), (XVII) and (XVIII).

PHARMACOLOGY

The efficacy of compounds of the present invention as both inotropic and beta-andrenergic blocking agents can be evaluated and measured using pharmacological methods known in the art or as described in detail below based on similarly established methodologies.

1. Rat Aorta Protocol

It has been shown by R. F. Kauffman et.al. in *J. of Pharmacol. Exp. Ther.* 242:864-872 (1987) that inotropic agents such as milrinone and enoximone produce marked relaxation of rat aorta. Such vasorelaxation appears to be related to inhibition of the phosphodiesterase (PDE) isozyme related to the cardiac sarcoplasmic reticulum. Thus, relaxation of rat aorta can be used as a screen to eliminate compounds which are not PDE inhibitors prior to testing for actual inotropic activity.

Rings of rat aorta (endothelium removed) were prepared for the measurement of isometric force in isolated tissue organ chambers essentially as previously described by T. J. Rimele et al in the *Journal of Pharmacol. Exo. Ther.* 245:102-111 (1988). The experimental portion of the protocol began with the addition of methylene blue ($1 \times 10^{-5}$M) and propranolol ($1 \times 10^{-6}$M) to each organ chamber to inhibit basal cGMP accumulation due to soluble guanylate cyclase and beta-adrenoceptors. Phenylephrine ($1 \times 10^{-7}$M) was then added and the rings were allowed to obtain a stable contractile response after which time, the test compound was added in a cumulative fashion. The relaxation induced by each concentration of the test compound was expressed as a percentage of the maximal relaxation produced by nitroprusside ($1 \times 10^{-4}$M). The results were graphically represented as a plot of the percentage relaxation vs. the negative log of the molar concentration of the test compound. The $IC_{50}$ (concentration of test compound which produced a relaxation equivalent to 50% of the maximal relaxation induced by nitroprusside) was determined for each tissue. The $IC_{50}$ for the compound of Example 2 was 23 micromolar with the maximal response being 97% at the highest dose tested (100 micromolar).

2. Anesthetized Dog

Inotropic effects were evaluated in barbiturate-anesthetized dogs by differentiating left intraventricular pressure. This procedure was carried out essentially as described by M. K. Grizzel et al in the FASEB Journal, Vol. 3, page 1039, abstract 4728 (1989). Purpose breed mongrel dogs (14-20 kg) of either sex were anesthetized with a mixture of sodium pentobarbital (15 mg/kg) and sodium barbital (300 mg/kg) i.v., intubated with a cuffed endotracheal tube and ventilated with a respirator (Harvard Apparatus, model 613, South Natick, Mass.) with room air (22 rpm, 10-12 ml/kg/stroke). A 5F pressure transducer (Millar Instruments, Mikkro-tip. Houston, Tex.) was inserted through the right carotid artery into the left ventricle to monitor intraventricular pressure. The left ventricular pressure signal was differentiated (using a 100Hz low pass differential amplifier, Gould Inc., Cleveland, Ohio) to obtain its maximal rate of rise (+dP/dt), and used to trigger a biotach amplifier to record heart rate. Cardiac output was determined via thermodilution with a Spectramed computer (Starcom., Oxnard, Calif.) and a 5F Swan Ganz catheter which was inserted into the right jugular vein and positioned in the pulmonary artery. The femoral artery was cannulated for monitoring arterial blood pressure with a pressure transducer (Micron model MP15D, Simi Valley, Calif.). A lead II electrocardiogram was measured using subcutaneous electrodes. Following surgery and instrumentation, each dog was placed in the left lateral decubitus position for the remainder of the experiment, and allowed to stabilize for 45-60 min before starting the experimental protocol. Rectal temperature was monitored and maintained at 37°-38° C. with a heating pad (Baxter Health Care model K20, McGaw Park, Ill.). All variables were recorded using a Gould 3800S physiograph.

Isoproterenol (0.1-0.5 μg/kg) was injected i.v. into the cephalic vein at 10 min intervals except for when the test drug infusion was begun. Four of these initial injections were made to establish the baseline response. Ten min after the forth isoproterenol injection an infusion of test compound was started at 0.01 micromol/kg/10 min after 10 min of test drug infusion an isoproterenol injection was made and the dose rate of test compound was increased. This process was continued up to a dose of test compound ranging from 300 to 10,000 micromol/kg total cumulative dose. Inhibition of the isoproterenol responses on contractility (dP/dt), heart rate and diastolic blood pressure were determined at each dose of test compound. The inotropic effect of each compound was determined by comparing the level of dP/dt at the end of each 10 min period to that of the level of dP/dt just prior to the infusion of test compound. The $ED_{50}$s were determined by a 2 point interpolation of the responses obtained that were just below and above 50% inhibition of the isoproterenol response or a 50% increase in dP/dt. Data are expressed in nanomol/kg.

Inotropic effects of the compounds were determined by changes in the baseline dP/dt whereas the beta-blocking effects of the compounds were determined by requanitating inhibition of the dP/dt response to isoproterenol. The compound of the invention of Example 2 showed an inotropic $ED_{50}$ of 40 nanomoles/kg, compared to a baseline established prior to drug infusion and an $ED_{50}$ for inhibition of the isoproterenol response of 55 nanomoles/kg. Further, as opposed to many prior inotropic agents which show partial beta agonism whereby the inotropic effects can be prevented by infusion of atenolol, the compound of formula (I) produced in Example 2 showed inotropic effects at higher doses which were not blocked by atenolol. In addition, many other inotropic agents whose inotropic effects at higher doses are not prevented by atenolol are phosphodiesterase inhibitors which do not have beta blocking properties.

3. Guinea Pig Left Atria Test

This test is carried out as generally described by T. P. Kenakin et al in Journal of Cardiovascular Pharmacology 101, 658-666 (1987) and in the Journal of Pharmacology and Experimental Therapeutics, Vol. 213, 406-413 (1980).

Male Hartley guinea-pigs (300-400 grams) were sacrificed by cervical dislocation or carbon dioxide asphyxiation. The hearts were immediately removed and placed in oxygenated Krebs-Henseleit buffer (composition (millimolar): $Na^+$ 143, $K^+$ 5.9, $Ca^{++}$ 1.25, $Mg^{++}$ 1.2, $Cl^-$ 128, $HCO_3^-$ 25, $SO_4^{--}$ 1.2, $H_2PO_4^-$ 1.0, and D-glucose 10). Left atria were dissected away from the remainder of the heart and mounted on holders against platinum punctate electrodes. The mounted atria were placed in tissue baths maintained at 31° C. and oxygenated with 95% $O_2$-5% $CO_2$ under 1.0 gram resting tension. The atria were stimulated through the punctate electrode and an external platinum electrode at the threshold voltage plus thirty percent, one Hertz frequency and five to ten milliseconds duration. Contractions were detected with a force displacement transducer and recorded on a physiograph.

The atria were allowed to equilibrate for at least one-half hr before the experimental compounds were added to the tissue baths. Propranolol (1.0 micromolar) and phentolamine (1.0 micromolar) were added to the buffer solution in the tissue baths to eliminate any effects of endogenous catecholamine release. Propranolol and phentolamine were added at least thirty min prior to the addition of the test compounds. During the equilibration period, the buffer solution was removed and replaced frequently. Phentolamine and propranolol were immediately re-introduced to the tissue baths after refilling with buffer.

Direct effects of the test compounds on the force of atrial contraction were observed and recorded after addition of the compounds to the tissue bath. Test compounds were added in concentrations from 1.0 to 100 micromolar in ten-fold increments (1.0, 10, 100 micromolar) with an additional concentration of 300 micromolar. Atria were exposed to each concentration of the test compounds until a constant response was observed. After a constant response was observed with the highest concentration (or five min in the absence of a response), forskolin was added in the presence of the test compound. Forskolin was added in ten-fold increments from 0.1 to 100 micromolar. Responses to the test compounds and forskolin were expressed as a percentage of the maximal response to forskolin. $EC_{50}$ values for the test compounds were calculated as the concentration of the compound necessary to produce an inotropic response half that of the maximal response produced by the test compound. For the compound produced in Example 2 the maximal response was 36% at 100 micromolar with an $ED_{50}$ of 13 micromolar concentration.

4. Beta Adrenoceptor Binding Assays

Because of its receptor density rat brain cortices were used as the source of membrane vesicles to be used in the receptor binding assays. Freshly excised cortexes were homogenized in 20 volumes (w/v) 50 mM TRIS HCl Buffer (pH 7.5), with a glass/Teflon homogenizer following the procedure previously described by T. J. Rimele in J. Pharmacol Exp. Ther. 239: 1-8, 1986. Beta-1 adrenoceptor binding activity was determined following methods described by M. H. Randall, et al, J. Med. Chem. 20: 1090-1094, 1977, and J. Homberger, et al in Mol. Pharmacol. 20: 453-469, 1981. The incubation mixture consisted of ; 26 $\mu$l of 50 mM TRIS/HCl, 10 mM $MgCl_2$ pH 7.6 buffer, 25 $\mu$l of test drug or 10-6 pindolol to define nonspecific binding, 100 $\mu$l of [I-125]-Pindolol (2200Ci/mM) at a final concentration of 10-9, and 100 $\mu$l of brain cortical membranes. The mixture was incubated at RT (22° C.) for two hr in the dark. The reaction was stopped by filtration of the mixture through buffer soaked glass fiber membranes (GF/B) using an cell harvesting device (Skatron Inc.). The radioactivity in each filter containing the trapped membrane particles was counted with a gamma counter. The value for non-specific binding in each assay was subtracted from total binding to give a value for specific binding. All specific binding values obtained in the presence of test compounds were expressed as the percentage of specific binding displaced by the individual agents. The resultant values were plotted on a log plot of concentration of test compound vs. percentage of displacement and an $IC_{50}$ value (drug concentration which produces 50% displacement) determined. Values obtained by this analysis are then reported as the negative log of the $IC_{50}$ ($pIC_{50}$). The compound of Example 2 showed a $pIC_{50}$ of 7.7.

Pharmaceutical Formulation and Doses

Compounds of the invention of formula (I) may be used in the treatment of CHF in a manner similar to the use of beta-adrenergic blocking agents and ($\pm$)-inotropic agents. After suffering a heart attack, one therapy which may be used is administration of a beta-blocker, such as atenolol to lessen oxygen consumption for the damaged heart muscle. However, there is often a negative inotropic action associated with beta-blockers whereby one may consider use of a positive inotropic agent. The usage of compounds of the invention may thus be correlated to the desire to manifest both beta-blocking and positive inotropic actions in a patient.

The compounds of the invention of formula (I) can be administered orally, topically or parenterally, e.g. rectal or i.v., of which the preferred route is oral. The compounds may be admixed with conventional tableting aids, diluents, excepients as known in the art to form tablets, capsules, powders, elixirs, liquids or suspensions as known in the pharmaceutical art. For administration to humans, the compounds of the invention may be administered in an amount of about 0.1 to 5 mg/kg about 1-4 times per day. The particular dosage will depend on the activity of the specific compound chosen and the severity of the physiological condition being treated. The projected dosage can be determined by correlation of test results in pharmacological tests for known positive inotropic agents such as milronone to those for compounds of formula (I).

In the following examples and throughout the specification, the following abbreviations may be used: g (grams),; mg (milligrams); l (liters); ml (milliliters); M (molar); mM (millimolar); i.v. (intraveneous); Hz (Hertz); dP/dt (change in pressure per time period); mol (moles); DMF (N,N-dimethylformamide); DMSO (dimethylsulfoxide); TFA (trifluoroacetic acid): RT (room temperature); EtOAc (ethyl acetate); min (minutes); hr (hours); m.p. (melting point); NMR (nuclear magnetic resonance); s (singlet); d (doublet); t (triplet); q(quartet); m (multiplet); and TLC (thin layer chromatography).

Unless otherwise indicated, all temperatures are expressed in ° C. (degrees Centigrade), pressures in mmHg (millimeters of mercury), NMR data in delta units and all references to ether are to diethyl ether.

EXAMPLE 1

5-{4-[N-[2-(3-Phenoxy-2-hydroxypropylamino)ethyl]-carbamoylmethoxy]phenyl}-6-methyl-2 -oxo-1,2-dihydro-3-pyridinecarbonitrile A dispersion of 177 mg (4.4 mmol) of 60% sodium hydride in mineral oil and 15 ml of DMF was treated, in portions, with 500 mg (2.2 mmol) of 5-(4-hydroxyphenyl)-6-methyl-2-oxo-1,2-dihydro-3-pyridinecarbonitrile (prepared according to method of G. Y. Lesher et al, U.S. Pat. No. 4,465,686). After the evolution of hydrogen ceases, the reaction is stirred 30 min at RT, then cooled in an ice bath. A solution of 440 mg (2.7 mmol) of ethyl bromoacetate in 1 ml of DMF is added dropwise. The reaction is stirred 30 min at 0° C., then 30 min at RT, and finally heated to 80° C. for 45 min. At this time TLC (95:5 $CHCl_3:CH_3OH$) indicated none of the starting phenol was present.

The mixture was concentrated under vacuum and the residue was taken up in 150 ml of EtOAc. The EtOAc was washed with water (3×75 ml) and the combined water washes acidified with 1N HCl, then extracted with EtOAc (3×75 ml). The combined EtOAc extracts are dried ($MgSO_4$), the solvent removed under vacuum, and the residue flash chromatographed on silica gel (98:2 $CHCl_3:CH_3OH$) to give 290 mg of 5-(4-carboethoxymethoxyphenyl)-6-methyl-2-oxo-1,2-dihydro-3-pyridinecarbonitrile as a white solid. $^1$H-NMR ($CDCl_3$): δ 1.35 (t, 3H); 2.50 (s, 3H); 4.35 (q, 2H); 4.70 (s, 2H); 7.00 (d, 2H); 7.20 (d, 2H); 7.85 (s, 1H). Yield, 42%.

A solution of 280 mg (0.90 mmol) of the ethyl ester prepared above in 10 ml of 1:1 ethanol:water containing 151 mg (2.7 mmol) of potassium hydroxide is heated with stirring under $N_2$ at 80° C. for 2 hr. The reaction is diluted with 3× its volume of water and extracted with ether (2×50 ml). The aqueous phase is cooled in ice and acidified with 6N HCl. The resulting precipitate is collected by suction filtration, washed with water, and dried in a vacuum oven at 80° C. overnight to give 250 mg of 5-(4-carboxymethoxyphenyl)-6-methyl-2-oxo-1,2,dihydro-3-pyridinecarbonitrile as a white solid. $^1$H-NMR ($d_6$-DMSO): δ 2.23 (s,3H); 4.70 (s,2H); 6.97 (d,2H); 7.25 (d,2H); 8.05 (s,1H).

A solution of 1.0 g (6.2 mmol) of 2-(tert-butoxycarbamoyl)ethylamine and 940 mg (6.2 mmol) of (±)-3-phenoxy-1,2-epoxypropane in 15 ml of methanol is heated at reflux under $N_2$ for 5 hr. After removing the solvent, the residue is flash chromatographed on silica gel (500 ml 98:2 $CHCl_3:CH_3OH$, 500 ml of 95:5 $CHCl_3:CH_3OH$, 500 ml of 90:10 $CHCl_3:CH_3OH$, and finally 1000 ml of 90:10:2 $CHCl_3:CH_3OH:NH_4OH$) to give 956 mg of (±)-N-(2-tertbutoxycarbamoylethyl)-2-hydroxy-3-phenoxypropylamine as a white solid. $^1$H-NMR ($CDCl_3$): δ 1:55 (s,9H); 2.58–3.03 (m,6H); 3.30 (m,2H); 4.00 (d,2H); 4.17 (m,1H); 5.00 (s broad, 1H); 6.97 (m,3H); 7.30 (m,2H). Yield, 50%.

A solution of 950 mg (3.1 mmol) of the carbamate prepared above in 10 ml of methylene chloride is cooled in an ice bath and treated with 10 ml of trifluoroacetic acid. After 1 hr the reaction is allowed to come to RT and stirred for 2 hr more. Volatiles are removed under vacuum and the residue taken up in 30 ml of acetonitrile, 1.69 g (12.2 mmol) of powdered anhydrous $K_2CO_3$ added, and the mixture stirred at 60° C. for 2 hr. After cooling, the mixture is filtered and the recovered solids are continuously extracted overnight in a soxhlet apparatus with acetonitrile. The acetonitrile from the filtration and the continuous extraction are combined and the solvent removed. The residue is flash chromatographed on silica gel (90:10:2 $CHCl_3:CH_3OH:NH_4OH$) to give 510 mg of (±)-N-(2-aminoethyl)2-hydroxy-3-phenoxypropylamine as a viscous oil. $^1$H-NMR ($CD_3OD$): δ 2.70 (m,6H); 3.93 (s,2H); 4.08 (m,1H); 4.90 (s,2H); 6.90 (m,3H); 7.22 (m,2H). Yield, 80%.

A solution of 500 mg (1.8 mmol) of 5-(4-carboxymethoxyphenyl)-6-methyl-2-oxo-1,2-dihydro-3-pyridinecarbonitrile (prepared as described above) and 407 mg (1.9 mmol) of (±)-N-(2-aminoethyl)-2-hydroxy-3-phenoxypropylamine (prepared as described above), and 316 mg (1.9 mmol) of diethyl cyanophosphonate in 10 ml of DMF is cooled in an ice bath and a solution of 540 μl (3.9 mmol) of triethylamine in 2 ml of DMF is added dropwise. The reaction is allowed to slowly come to RT and is stirred overnight under $N_2$. The volatiles are removed under vacuum and the residue is flash chromatographed on silica gel (90:10:2 $CHCl_3:CH_3OH:NH_4OH$) to give a white solid. This solid is recrystallized from EtOAc:methanol to give 185 mg of 5-{4-[N-[2-(3-phenoxy-2-hydroxypropylamino)ethyl]carbamoylmethoxy]phenyl}-6-methyl-2-oxo-1,2-dihydro-3-pyridinecarbonitrile as a white solid, m.p. 136°–138° C. Yield, 21%. Elemental Analysis (for $C_{26}H_{28}N_4O_5.0.5 H_2O$):

|  | % C | % H | % N |
| --- | --- | --- | --- |
| Found: | 64.63 | 5.94 | 11.44 |
| Calculated: | 64.31 | 6.02 | 11.54 |

EXAMPLE 2

5-{4-[N-[2-(3-Phenoxy-2-hydroxypropylamino)ethyl]-carbamoylpropyloxy]phenyl}-6-methyl-2-oxo-1,2-dihydro-3-pyridinecarbonitrile A dispersion of 420 mg (177 mmol) of 60% sodium hydride in mineral oil and 35 ml of DMF is treated, in portions, with 2.00 g (8.8 mmol) of 5-(4-hydroxyphenyl)-6-methyl-2-oxo-1,2-dihydro-3-pyridinecarbonitrile. After 30 min of stirring at RT, the reaction is cooled in an ice bath and a solution of 1.72 g (8.8 mmol) of ethyl 4-bromobutyrate in 5 ml of DMF is added dropwise. The reaction is allowed to slowly warm to RT, then heated at 60° C. for 2 hr. Volatiles are removed under vacuum and the residue taken up in 100 ml of 1:1 EtOAc-water. Upon standing for 1 hr at RT, a solid precipitate forms. This solid is collected by suction filtration, washed thoroughly with water and EtOAc, and dried in a vacuum oven at 80° C. to give 1.50 g of a light yellow solid. The aqueous phase is extracted with EtOAc (2×50 ml), dried (MgSO$_4$), and the solvent removed to leave about 400 mg of a solid. This solid is washed with EtOAc and filtered to give 250 mg of a pale yellow solid. These two solids were combined to give 1.750 g of 5-(4-carboethoxypropyloxyphenyl)-6-methyl-2-oxo-1,2-dihydro-3-pyridinecarbonitrile as a pale yellow solid, m.p. 222°–224° C. $^1$H-NMR (d$_6$-DMSO): δ 1.20 (t,3H); 1.95 (m,2H); 2.05 (s,3H); 2.43 (t,2H); 4.03 (m,4H); 6.95 (d,2H); 7.25 (d,2H); and 8.00 (s,1H). Yield, 58%.

A solution of 1.50 g (4.4 mmol) of the ethyl ester prepared above in 70 ml of 1:1 ethanol:water containing 740 mg (13.2 mmol) of potassium hydroxide is heated at 60° C. for 2 hr under N$_2$. The reaction mixture is concentrated to ½ volume under vacuum, diluted with 75 ml of water, and extracted with EtOAc (2×75 ml). The aqueous layer is acidified with 10% HCl, and the solid which precipitates out is collected by suction filtration. This solid is washed thoroughly with water and dried at 100° C. overnight to give 1.32 g of 5-(4-carboxypropyloxyphenyl)-6-methyl-2-oxo-1,2-dihydro-3-pyridinecarbonitrile as a white solid, m.p. 247°–249° C. $^1$H-NMR (d$_6$-DMSO); δ 1.90 (m,2H); 2.40 (t,2H); 4.05 (t,2H); 6.95 (d,2H); 7.25 (d,2H); 8.05 (s,1H). Yield, 96%.

A solution of 500 mg (1.6 mmol) of 5-(4-carboxypropyloxyphenyl)-6-methyl-2-oxo-1,2-dihydro-3-pyridinecarbonitrile, 370 mg (1.8 mmol) of (±)-N-(2-aminoethyl)-2-hydroxy-3-phenoxypropylamine (prepared as described in Example 1), and 290 mg (1.8 mmol) of diethyl cyanophosphonate in 8 ml of DMF is stirred under N$_2$ while cooling in an ice bath. A solution of 270 μl (1.94 mmol) of triethylamine in 2 ml of DMF is added dropwise. The reaction is allowed to slowly come to RT and is stirred overnight. Volatiles are removed under vacuum and the residue is flash chromatographed on silica gel (90:10:2 CHCl$_3$:CH$_3$OH:NH$_4$OH) to give a white solid. This solid is recrystallized from methanol to give 320 mg of 5-{4-[N-[2-(3-phenoxy-2-hydroxypropylamino)ethyl]carbamoylpropyloxy]phenyl}-6-methyl-2-oxo-1,2-dihydro-3-pyridinecarbonitrile as a white solid, m.p. 170°–171.5° C. Yield, 40% Elemental Analysis (for C$_{28}$H$_{32}$N$_4$O$_5$)

|  | % C | % H | % N |
|---|---|---|---|
| Found: | 66.57 | 6.40 | 11.07 |
| Calculated: | 66.65 | 6.39 | 11.10 |

EXAMPLE 3

5-{4-[N-[3-Phenoxy-(2S)-hydroxypropyl]aminopropyloxy]phenyl}-6-methyl-2-oxo-1,2-dihydro-3-pyridinecarbonitrile A solution of 2.00 g (8.84 mmol) of 5-(4-hydroxyphenyl)-6-methyl-2-oxo-1,2-dihydro-3-pyridinecarbonitrile in 15 ml of DMF is added dropwise to a suspension of 707 mg (17.7 mmol) of 60% sodium hydride-mineral oil in DMF (5 ml). When hydrogen evolution ceases, the mixture is warmed to 60° C. and a solution of 2.37 g (8.84 mmol) of N-(3-bromopropyl)phthalimide in 5 ml of DMF is added dropwise. After 1 hr at 60° C., the temperature of the mixture is raised to 80° C. for an additional hr of heating. After cooling, the DMF is removed under vacuum. The residue is triturated with water and EtOAc to give a yellow solid that is collected by suction filtration. This solid is dried at 80° C. under vacuum to give 1.885 g of 5-(4-phthalimidopropyloxyphenyl)-6-methyl-2-oxo-1,2-dihydro-3-pyridinecarbonitrile as a yellow solid. $^1$H-NMR (d$_6$-DMSO): δ 2.07 (t,2H); 2.23 (s,3H); 3.78 (t,2H); 4.05 (t,2H); 6.83 (d, 2H); 7.20 (d,2H): 7.80 (m, 4H); 8.00 (s, 1H).

A solution of 1.885 g (4.70 mmol) of 5-(4-phthalimidopropyloxyphenyl)-6-methyl-2-oxo-1,2-dihydro-3-pyridinecarbonitrile and 251 μl (5.17 mmol) of hydrazine monohydrate in 50 ml of ethanol is heated 16 hr at reflux. The volatiles are removed under vacuum and the residue is taken up in 15 ml of 1:1 CHCl$_3$:CH$_3$ and flash chromatographed through a 6 inch length column of silica gel (90:10:2 CHCl$_3$:CH$_3$OH:NH$_4$OH). The solid obtained form the chromatography is recrystallized from CHCl$_3$:CH$_3$OH to give 901 mg of 5-(4-aminopropyloxyphenyl)-6-methyl-2-oxo-1,2-dihydro-3-pyridinecarbonitrile as a yellow powder. $^1$H-NMR (d$_6$-DMSO): δ 1.80 (t,2H); 2.73 (t,2H); 3.70 (s broad, 2H); 4.03 (t,2H); 6.92 (d,2H); 7.20 (d,2H); 7.85 (s, 1H).

A solution of 500 mg (1.76 mmol) of 5-(4-aminopropyloxyphenyl)-6-methyl-2-oxo-1,2-dihydro-3-pyridinecarbonitrile and 166 μl (1.23 mmol) of (2S)-3-phenoxy-1,2-epoxypropane (prepared according to the procedure of K. B. Sharpless et al, J. Org. Chem; 1989, 54, 1302) in 10 ml of DMSO is heated 6 hr at 90° C. under N$_2$. Solvent is removed under vacuum and the residue boiled with 50 ml of 1:1 CHCl$_3$:CH$_3$OH, cooled to RT and filtered to remove 124 mg of unreacted starting amine. The filtrate is flash chromatographed through silica gel (90:10:2 CHCl$_3$:CH$_3$OH:NH$_4$OH) to give 312 mg of crude product. After recrystallization from EtOAc-methanol, 208 mg of 5-{4-[N-[3-phenoxy-(2S)-hydroxypropyl]aminopropyloxy]phenyl}-6-methyl-2-oxo-1,2-dihydro-3-pyridinecarbonitrile is obtained as a pale yellow solid, m.p. 141°–143° C. Yield, 39%. Elemental Analysis (for C$_{25}$H$_{27}$N$_3$O$_4$):

|  | % C | % H | % N |
|---|---|---|---|
| Found: | 68.97 | 6.33 | 9.59 |
| Calculated: | 69.26 | 6.28 | 9.69 |

EXAMPLE 4

5-{3-[N-[2-(3-Phenoxy-2-hydroxypropylamino)ethyl]-carbamoylmethoxy]phenyl}-6-methyl-2-oxo-1,2-dihydro-3-pyridinecarbonitrile A dispersion of 530 mg (22.2 mmol) of 60% sodium hydride in mineral oil and 5 ml of DMF was treated dropwise with a solution of 2.500 g (11.1 mmol) of 5-(3-hydroxyphenyl)-6-methyl-2-oxo-1,2-dihydro-3-pyridinecarbonitrile (prepared according to the method of G. Y. Lesher et al, U.S. Pat. No. 4,465,686). The reaction is stirred 30 min at RT, then cooled in an ice bath and a solution of 1.840 g (11.1 mmol) of ethyl bromoacetate in 5 ml of DMF is added dropwise. The reaction is stirred for 30 min at 0° C., then 30 min at RT. The reaction mixture is concentrated under vacuum and the residue taken up in 100 ml of water and 200 ml of EtOAc. The aqueous layer is acidified to pH=5 and extracted with EtOAc (3×200 ml). The EtOAc is dried (MgSO$_4$) and concentrated to about ¼ volume under vacuum. The light yellow solid precipitate is collected by suction filtration (1.90 g). The filtrate is concentrated under vacuum and the residue flash chromatographed on silica gel (98:2 CHCl$_3$:CH$_3$OH) to give an additional 0.55 g of product. Total yield of 5-(3-carboethoxymethoxyphenyl)-6-methyl-2-oxo-1,2-dihydro-3-pyridinecarbonitrile is 2.45 g of pale yellow solid. Yield, 70%. $^1$H-NMR (CDCl$_3$): δ 1.35 (t,3H); 2.50 (s,3H); 4.30 (q,2H); 4.70 (s,2H); 6.85 (m,3H); 7.42 (t,1H); 7.90 (s,1H).

A solution of 2.40 g (7.7 mmol) of the ethyl ester prepared above in 80 ml of 1:1 ethanol:water containing 1.52 g (23.1 mmol) of potassium hydroxide is stirred under N$_2$ at RT over night. The mixture is then heated at 60° C. for 2 hr. After cooling, the reaction is concentrated to ½ its original volume, diluted with 100 ml of water, and extracted with EtOAc (3×100 ml). The aqueous phase is acidified with 6N HCl, the resulting precipitate collected by suction filtration, washed with water, and dried under vacuum at 80° C. to give 2.1 g of 5-(3-carboxymethoxyphenyl)-6-methyl-2-oxo-1,2-dihydro-3-pyridinecarbonitrile as a white solid. Yield, 95%. $^1$H-NMR (d$_6$-DMSO): δ 2.25 (s,3H); 4.70 (s,2H); 6.90 (m,3H); 7.30 (m,1H); 8.08 (s,1H).

A solution of 500 mg (1.8 mmol) of 5-(3-carboxymethoxyphenyl-6-methyl-2-oxo-1,2-dihydro-3-pyridinecarbonitrile (prepared as described above) and 407 mg (1.9 mmol) of (±)-N-(2-aminoethyl)-2-hydroxy-3-phenoxypropylamine (as described in Example 1) and 316 mg (1.9 mmol) of diethylcyanophosphonate in 10 ml of DMF is cooled in an ice bath and a solution of 540 μl (3.9 mmol) of triethylamine in 2 ml of DMF is added dropwise. The reaction is allowed to slowly come to RT and is stirred overnight under N$_2$. The mixture is concentrated under vacuum and the residue flash chromatographed on silica gel (90:10:2 CHCl$_3$:CH$_3$OH:NH$_4$OH) to give 310 mg of 5-{3-[N-[2-(3-phenoxy-2-hydroxypropylamino)ethyl]carbamoylmethoxy]phenyl}-6-methyl-2-oxo-1,2-dihydro-3-pyridinecarbonitrile as a white solid, m.p. 194°–196.5° C. Yield, 37%. Elemental Analysis (for C$_{26}$H$_{28}$N$_4$O$_5$):

|  | % C | % H | % N |
|---|---|---|---|
| Found: | 65.36 | 5.99 | 11.66 |
| Calculated | 65.53 | 5.92 | 11.76 |

EXAMPLE 5

5-{3-[N-[2-(3-Phenoxy-2-hydroxypropylamino)ethyl]-carbamoylpropyloxy]phenyl}-6-methyl-2-oxo-1,2-dihydro-3-pyridinecarbonitrile A dispersion of 337 mg (14.0 mmol) of 60% sodium hydride in mineral oil and 5 ml of DMF is treated, dropwise, with a solution of 1.60 g (7.0 mmol) of 5-(3-hydroxyphenyl)-6-methyl-2-oxo-1,2-dihydro-3-pyridinecarbonitrile. The reaction is stirred 30 min at RT, then cooled in an ice bath and 1.36 g (7.0 mmol) of ethyl 4-bromobutyrate in 5 ml of DMF is added dropwise. The reaction is allowed to slowly come to RT and stirred over night. The mixture is concentrated under vacuum, the residue is taken up in 80 ml of water, extracted with EtOAc, acidified to pH=5 with 1N HCl, and the aqueous phase extracted with EtOAc (4×80 ml). The EtOAc is dried (MgSO$_4$) and the solvent removed to leave a light yellow solid. This solid is triturated with hot ether and filtered to give 1.40 g of 5-(3-carboethoxypropyloxyphenyl)-6-methyl-2-oxo-1,3-dihydro-3-pyridinecarbonitrile as a pale yellow solid, m.p. 168°–169° C. $^1$H-NMR (d$_6$-DMSO): δ 1.20 (t,3H); 1.95 (m,2H); 2.15 (s,3H); 2.50 (t,2H); 4.03 (q,2H); 4.05 (t,2H); 6.95 (m,3H); 7.30 (m,1H); 8.10 (s,1H).

A solution of 1.40 g (4.1 mmol) of the ethyl ester prepared above in 70 ml of 1:1 ethanol:water containing 814 mg (12.3 mmol) of potassium hydroxide is stirred under N$_2$ over night at RT. The mixture is then concentrated under vacuum and the residue diluted with 50 ml of water and extracted with EtOAc (2×25 ml). The aqueous layer is acidified with 10% HCl to produce a light yellow solid. The solid is collected by suction filtration, washed with water (2×50 ml) and ether (2×50 ml), then dried overnight under vacuum at 90° C. to give 1.22 g of 5-(3-carboxypropoxyphenyl)-6-methyl-2-oxo-1,2-dihydro-3-pyridinecarbonitrile as a pale yellow solid, m.p. 217.5°–219.5° C. Yield, 95%. $^1$H-NMR: (d$_6$-DMSO): δ 1.95 (m,2H); 2.25 (s,3H); 2.40 (t,2H); 4.02 (t,2H); 6.90 (m,3H); 7.30 (t,1H); 8.10 (s,1H).

A solution of 730 mg (2.3 mmol) of 5-(3-carboxypropoxyphenyl)-6-methyl-2-oxo-1,2-dihydro-3-pyridinecarbonitrile (prepared as described above), 590 mg (2.8 mmol) of (±)-N-(2-aminoethyl)-2-hydroxy-3-phenoxypropylamine (as described in Example 1), and 420 mg (2.6 mmol) of diethylcyanophosphonate in 20 ml of DMF is cooled in an ice bath and a solution of 390 μl (2.80 mmol) of triethylamine in 5 ml of DMF is added dropwise. The reaction is allowed to slowly come to RT and stirred overnight under N$_2$. Volatiles are removed under vacuum and the residue is flash chromatographed on silica gel (90:10:2 CHCl$_3$:CH$_3$OH:NH$_4$OH) to give 550 mg of 5-{3-[N-[2-(3-phenoxy-2-hydroxypropylamino)ethyl]carbamoylpropoxy]phenyl}-6-methyl-2-oxo-1,3-dihydro-3-pyridinecarbonitrile as a white solid, m.p. 134°–138° C. Elemental Analysis (for C$_{28}$H$_{32}$N$_4$O$_5$.0.5H$_2$O):

|  | % C | % H | % N |
|---|---|---|---|
| Found: | 66.02 | 6.31 | 10.94 |
| Calculated: | 65.48 | 6.28 | 10.91 |

EXAMPLE 6

5-{2-[N-[2-(3-Phenoxy-2-hydroxypropylamino)ethyl]-carbamoylmethoxy]phenyl}-6-methyl-2-oxo-1,2-dihydro-3-pyridinecarbonitrile A dispersion of 530 mg of 60% sodium hydride in mineral oil and 10 ml of DMF is treated, dropwise, with a solution of 1.50 g (6.6 mmol) of 5-(2-hydroxyphenyl)-6-methyl-2-oxo-1,2-dihydro-3-pyridinecarbonitrile in 20 ml of DMF. The reaction is stirred 30 min at RT, then cooled in an ice bath and 1.11 g (6.6 mmol) of ethyl bromoacetate in 30 ml of DMF is added dropwise. The reaction is allowed to slowly come to RT and stirred overnight under $N_2$. The mixture is concentrated under vacuum, the residue taken up in 80 ml of water and extracted with EtOAc. The aqueous phase is acidified to pH=5 with 10% HCl and extracted with EtOAc (4×80 ml). The combined EtOAc extracts are dried ($MgSO_4$) and the solvent removed to leave an orange solid. This solid is recrystallized from EtOAc to give 740 mg of 5-(2-carboethoxymethoxyphenyl)-6-methyl-2-oxo-1,2-dihydro-3-pyridinecarbonitrile as a yellow solid, m.p. 188°–190° C. Yield, 37%. $^1$H-NMR ($d_6$-DMSO): δ 1.20 (t,3H); 2.18 (s,3H); 4.15 (q,2H); 4.80 (s,2H); 7.0 (q,2H); 7.20 (d,1H); 7.35 (t,1H); 8.00 (s,1H).

A solution of 730 mg (2.3 mmol) of the ethyl ester prepared above in 60 ml of 1:1 ethanol:water containing 460 mg (7.0 mmol) of potassium hydroxide is heated at 60° C. under $N_2$ for 2 hr. The mixture is then concentrated under vacuum to ⅓ volume, 50 ml of water added, and the mixture extracted with EtOAc (2×25 ml). The aqueous phase is acidified to a pH=5 with 10% HCl and the resulting precipitate collected by suction filtration. The precipitate is washed with water and dried at 90° C. under vacuum to give 620 mg of 5-(2-carboxymethoxyphenyl)-6-methyl-2-oxo-1,2-dihydro-3-pyridinecarbonitrile as a pale yellow solid, m.p. 297°–299° C. Yield, 95%. $^1$H-NMR ($d_6$-DMSO): δ 2.18 (s,3H); 4.70 (s,2H); 7.00 (q,2H); 7.21 (d, 1H); 7.38 (t, 1H); 8.00 (s,1H).

A solution of 500 mg (1.8 mmol) of 5-(2-carboxymethoxyphenyl)-6-methyl-2-oxo-1,2-dihydro-3-pyridinecarbonitrile (prepared as described above), 407 mg (1.9 mmol) of (±)-N-(2-aminoethyl)-2-hydroxy-3-phenoxypropylamine (prepared as described in Example 1), and 316 mg (1.9 mmol of diethylcyanophosphonate in 10 ml of DMF is cooled in an ice bath and a solution of 540 μl (1.9 mmol) of triethylamine in 2 ml of DMF is added dropwise. The reaction is allowed to come to RT and stirred overnight under $N_2$. The mixture is concentrated under vacuum and the residue flash chromatographed on silica gel (90:10:2 $CHCl_3:CH_3OH:NH_4OH$) to give a yellow solid. This solid is recrystallized from EtOAc to give 190 mg of 5-{2-[N-[2-(3-phenoxy-2-hydroxypropylamino)ethyl]-carbamoylmethoxy]phenyl}-6-methyl-2-oxo-1,2-dihydro-3-pyridinecarbonitrile as a light yellow solid, m.p. 138°–141° C. Yield, 22%. Elemental Analysis (for $C_{26}H_{28}N_4O_5$):

EXAMPLE 7

5-{2-[N-[2-(3-Phenoxy-2-hydroxypropylamino)ethyl]-carbamoylpropyloxy]phenyl}-6-methyl-2-oxo-1,2-dihydro-3-pyridinecarbonitrile A dispersion of 780 mg (17.7 mmol) of 60% sodium hydride in mineral oil and 10 ml of DMF is treated, dropwise, with a solution of 2.00 g (8.8 mmol) of 5-(2-hydroxyphenyl)-6-methyl-2-oxo-1,2-dihydro-3-pyridine carbonitrile in 20 ml of DMF. The reaction is stirred 30 min at RT, then cooled in an ice bath and 1.72 g (8.8 mmol) of ethyl 4-bromobutyrate in 10 ml of DMF is added dropwise. The reaction is allowed to slowly come to RT and stirred overnight under $N_2$. The mixture is then concentrated under vacuum, the residue taken up in 80 ml of water, and extracted with EtOAc (2×25 ml). The aqueous phase is acidified to pH=5 with 10% HCl and extracted with EtOAc (4×80 ml). The EtOAc extracts are dried ($MgSO_4$) and the solvent removed to leave an orange oil. This oil is crystallized from EtOAc-hexane to give 1.61 g of 5-(2-carboethoxypropyloxyphenyl)-6-methyl-2-oxo-1,2-dihydro-3-pyridinecarbonitrile as a light yellow solid, m.p. 167°–170° C. Yield, 54%. $^1$H-NMR ($d_6$-DMSO): δ 1.18 (t,3H); 1.88 (m,2H); 2.10 (s, 3H); 2.37 (t, 2H); 3.97 (q,2H); 7.00 (t,2H); 7.10 (d,1H); 7.20 (d,1H); 7.40 (t,1H); 7.97 (s,1H).

A solution of 1.50 g (4.4 mmol) of the ethyl ester prepared above in 70 ml of 1:1 ethanol:water containing 1.16 g (17.6 mmol) of potassium hydroxide is stirred overnight at RT under $N_2$. The reaction mixture is concentrated to ⅓ volume under vacuum, diluted with 50 ml of water, and extracted with EtOAc (2×25 ml). The aqueous phase is acidified to pH=5 with 10% HCl which causes a solid to precipitate out. This solid is collected by suction filtration, washed with water, then ether, and dried over night under vacuum at 90° C. to give 1.32 of 5-(2-carboxypropyloxyphenyl)-6-methyl-2-oxo-1,2-dihydro-3-pyridinecarbonitrile as a light yellow solid, m.p. 228°–230° C. Yield, 96%. $^1$H-NMR ($d_6$-DMSO): δ 1.83 (m,2H); 2.08 (s, 3H); 2.25 (t,2H); 3.98 (t,2H); 7.00 (t,1H); 7.10 (d,1H); 7.20 (d,1H); 7.35 (t,1H); 7.97 (s,1H).

A solution of 700 mg (2.2 mmol) of 5-(2-carboxypropyloxyphenyl)-6-methyl-2-oxo-1,2-dihydro-3-pyridinecarbonitrile (prepared as described above), 580 mg (2.8 mmol) of (±)-N-(2-aminoethyl)-2-hydroxy-3-phenoxypropylamine (prepared as described in Example 1), and 420 mg (2.6 mmol) of diethylcyanophosphonate in 20 ml of DMF is cooled in an ice bath. A solution of 390 μl (2.6 mmol) of triethylamine in 5 ml of DMF is added dropwise, and the reaction allowed to come to RT and stirred overnight. The mixture is concentrated under vacuum and the residue flash chromatographed on silica gel to give a light yellow solid. This solid is recrystallized from EtOAc to give 440 mg of 5-{2-[N-[2-(3-phenoxy-2-hydroxypropylamino)ethyl]carbamoylpropyloxy]phenyl}-6-methyl-2-oxo-1,2-dihydro-3-pyridinecarbonitrile as a light yellow solid, m.p. 150°–153° C. Elemental Analysis (for $C_{28}H_{32}N_4O_5$):

|  | % C | % H | % N |
|---|---|---|---|
| Found: | 65.01 | 6.14 | 11.39 |
| Calculated: | 65.53 | 5.92 | 11.76 |

|  | % C | % H | % N |
|---|---|---|---|
| Found: | 66.25 | 6.42 | 11.00 |
| Calculated: | 66.65 | 6.39 | 11.10 |

EXAMPLE 8

5-{4-[N-[2-[3-(2-Cyanophenoxy)-2S-hydroxypropylamino]-2-methylpropyl]carbamoylpropyloxy]phenyl-6-methyl-2-oxo-1,2-dihydro-3-pyridinecarbonitrile A solution of 820 mg (2.6 mmol) of 5-(4-carboxypropyloxyphenyl)-6-methyl-2-oxo-1,2-dihydro-3-pyridinecarbonitrile (prepared as described in Example 2 above), 750 μl (5.38 mmol) of triethylamine, and 15 ml of DMF is cooled in an ice-water bath while stirring under $N_2$. A solution of 540 mg (3.9 mmol) of isobutyl chloroformate in 5 ml of DMF is added dropwise. After 4 hr of stirring at 0° C., the reaction mixture is poured into water (75 ml), and extracted with EtOAc (2×50 ml). The combined EtOAc extracts are washed with water, dried (MgSO₄), filtered and the solvent removed to leave 800 mg of 5-(4-isobutyloxycarbonyloxycarbonylpropoxyphenyl)-6-methyl-2-oxo-1,2-dihydro-3-pyridinecarbonitrile as a tan-colored solid. $^1$H-NMR (CDCl₃): δ 1.00 (d, 6H); 1.60 (m, 1H); 2.16 (m, 2H); 2.50 (s, 3H); 2.70 (t, 2H); 4.10 (m, 4H); 6.93 (d, 2H); 7.20 (d, 2H); 7.80 (s, 2H).

The mixed anhydride prepared above (800 mg, 1.9 mmol) in 25 ml of chloroform containing 510 mg (5.79 mmol) of 1,2-diamino-2-methylpropane is heated at reflux overnight under $N_2$. The mixture is concentrated under vacuum and purified by flash chromatography on silica gel (90:10:2 CHCl₃:CH₃OH:NH₄OH) to give a tacky solid. This solid is recrystallized from EtOAc to give 295 mg of 5-{4-[N-[2-amino-2-methylpropyl]carbamoylpropyloxy]phenyl}-6-methyl-2-oxo-1,2-dihydro-3-pyridinecarbonitrile as a white solid, m.p. 187.5°–189.0° C. $^1$H-NMR (d₆-DMSO): δ 0.96 (s, 6H); 1.93 (m, 2H); 2.20 (s, 3H); 2.30 (t, 2H); 2.95 (d, 2H); 3.98 (t, 2H); 6.93 (d, 2H); 7.21 (d, 2H); 7.80 (t, 1H); 7.93 (s, 1H).

A solution of 270 mg (0.70 mmol) of the amine prepared above is dissolved in. 1 ml of DMSO by warming. A solution of 111 mg (0.63 mmol) of (2S)-3-(2-cyanophenoxy)-1,2-epoxypropane in 4 ml of methanol is added and the mixture heated at reflux overnight under $N_2$. The mixture is concentrated under vacuum and the residue flash chromatographed on silica gel (90:10 CHCl₃:CH₃OH) to give 90 mg of the title product as a pale yellow solid, m.p. 90°–98° C. Elemental Analysis (for $C_{31}H_{35}N_5O_5.H_2O$):

|  | % C | % H | % N |
|---|---|---|---|
| Found: | 64.84 | 6.41 | 12.37 |
| Calculated: | 64.67 | 6.47 | 12.16 |

EXAMPLE 9

5-{4-[N-3-(2-Cyanophenoxy)-(2S)-hydroxypropyl]aminopropyloxy]phenyl)-6-methyl-2-oxo-1,2-dihydro-3-pyridinecarbonitrile A solution of 500 mg (1.8 mmol) of 5-(4-aminopropyloxyphenyl)-6-methyl-2-oxo-1,2-dihydro-3-pyridinecarbonitrile (prepared as in Example 3) and 275 mg (1.6 mmol) of (2S)-3-(2-cyanophenoxy)-1,2-epoxypropane (prepared from 2-cyanophenol according to the procedure of K. B. Sharpless et al, J. Org. Chem 1989, 54, 1302) in 10 ml of methanol is heated at reflux under $N_2$ for 5 hr. The methanol is removed under vacuum and the residue flash chromatographed on silica gel (250 ml 95:5 CHCl₃:CH₃OH then 500 ml of 90:10 CHCl₃:CH₃OH) to afford 120 mg of the title compound as a pale yellow solid, m.p. 145°–152° C. Yield, 16%. Elemental Analysis (for $C_{26}H_{26}N_4O_4.H_2O$):

|  | % C | % H | % N |
|---|---|---|---|
| Found: | 65.93 | 5.79 | 11.66 |
| Calculated: | 65.53 | 5.92 | 11.75 |

EXAMPLE 10

5-{4-[N-[2-[3-(2-Chlorophenoxy)-2S-hydroxypropylamino]-2-methylpropyl]carbamoylpropyloxy]phenyl-6-methyl-2-oxo-1,2-dihydro-3-pyridinecarbonitrile A mixture of 2.30 g (7.4 mmol) of 5-(4-carboxypropyloxyphenyl)-6-methyl-2-oxo-1,2-dihydro-3-pyridinecarbonitrile (prepared as described in Example 2), 1.12 ml (8.0 mmol) of triethylamine, 1.32 g (8.1 mmol) of diethyl cyanophosphonate, and 710 mg (8.10 mmol) of 2-methyl-1,2-diaminopropane in 60 ml of DMF is stirred under $N_2$ in an ice water bath for 1 hr, then allowed to come to RT and stirred overnight. The mixture is concentrated under vacuum and the residue is flash chromatographed on silica gel (90:10:2 CHCl₃:CH₃OH:NH₄OH) to give 2.00 g of crude product. After recrystallization from EtOAc, 1.20 g of 5-{4-[N-[2-amino-2-methylpropyl]carbamoylpropyloxy]phenyl}-6-methyl-2-oxo-1,2-dihydro-3-pyridinecarbonitrile as a white solid, m.p. 188°–189° C., is obtained. Yield, 42%.

A solution of 400 mg (1.0 mmol) of the amine prepared above and 193 mg (1.0 mmol) of (2S)-3-(2-chlorophenoxy)-1,2-epoxypropane in 10 ml of methanol and 1 ml of DMSO is heated overnight at reflux under $N_2$. The solvent is removed under vacuum and the residue is flash chromatographed on silica gel (90:10 CHCl₃:CH₃OH) to give 120 mg of the title compound as a pale yellow powder, m.p. 83°–91° C. Yield, 21%. Elemental Analysis (for $C_{30}H_{35}ClN_4O_5.H_2O$)

|  | % C | % H | % N |
|---|---|---|---|
| Found: | 61.72 | 6.35 | 9.46 |
| Calculated: | 61.58 | 6.37 | 9.57 |

EXAMPLE 11

5-{4-[N-[2-[3-(2-Cyanophenoxy)-2S-hydroxypropylamino]-2-methylpropyl]carbamoylmethoxy]phenyl-6-methyl-2-oxo-1,2-dihydro-3-pyridinecarbonitrile A mixture of 2.65 g (9.3 mmol) of 5-(4-carboxymethoxyphenyl)-6-methyl-2-oxo-1,2-dihydro-3-pyridinecarbonitrile (prepared as described in Example 1), 900 mg (10.3 mmol) of 1,2-diamino-2-methylpropane, and 1.67 g (10.3 mmol) of diethylcyanophosphonate in 30 ml of DMF is cooled with stirring under $N_2$ in an ice bath to ≈0° C. A solution of 1.5 ml (10.8 mmol) of triethylamine in 10 ml of DMF is added dropwise. The reaction mixture is allowed to come to RT and stirred overnight. Solvent is removed under vacuum and the residue flash chromatographed on silica gel (90:10:2 CHCl₃:CH₃OH:NH₄OH) to afford 2.8 g of crude product. After recrystallization from methanol-EtOAc 2.1 g of 5-{4-[N-[2-amino-2-methylpropyl]carbamoylmethoxy]phenyl-6-methyl-2-oxo-1,2-dihydro-3- pyridinecarbonitrile is obtained as a light yellow solid. Yield, 64%.

A solution of 400 mg (1.10 mmol) of the amine prepared above and 198 mg (1.10 mmol) of (2S)-3-(2-cyanophenoxy)-1,2-epoxypropane in 10 ml of methanol is heated overnight at 60° C. under $N_2$. Solvent is removed under vacuum and the residue flash chromatographed on silica gel (90:10 $CHCl_3$:$CH_3OH$) to give 190 mg of the title compound as a pale yellow solid, m.p. 93°–100° C. Elemental Analysis (for $C_{29}H_{31}N_5O_5.H_2O$):

|  | % C | % H | % N |
|---|---|---|---|
| Found: | 63.76 | 6.09 | 12.69 |
| Calculated: | 63.60 | 6.07 | 12.79 |

EXAMPLE 12

5-{4-[N-[2-[3-(2-Chlorophenoxy)-2S-hydroxypropylamino]-2-methylpropyl]carbamoylmethoxyphenyl-6-methyl-2-oxo-1,2-dihydro-3-pyridinecarbonitrile A solution of 400 mg (1.10 mmol) of 5-{4-[N-[2-amino-2-methylpropyl]carbamoylmethoxy]phenyl}-6-methyl-2-oxo-1,2-dihydro -3-pyridinecarbonitrile (prepared as described in Example 11) and 208 mg (1.10 mmol) of (2S)-3-(2-chlorophenoxy)-1,2-epoxypropane in 10 ml of methanol is heated overnight at 60° C. under $N_2$. A solid which precipitates is removed by filtration (70 mg of starting amine). The filtrate is concentrated under vacuum and the residue flash chromatographed on silica gel (90:10 $CHCl_3$:$CH_3OH$) to give 227 mg of crude product. After recrystallization from EtOAc-hexane, 170 mg of the title compound is obtained as a pale yellow solid, m.p. 86°–93° C. Elemental Analysis (for $C_{28}H_{31}ClN_4O_5.\frac{1}{2} H_2O$):

|  | % C | % H | % N |
|---|---|---|---|
| Found: | 61.19 | 6.04 | 10.20 |
| Calculated: | 61.36 | 5.89 | 10.22 |

EXAMPLE 13

5-{4-[N-2-[3-(2-Cyano-5-chlorophenoxy)-2S-hydroxypropylamino]-2-methylpropyl]carbamoylmethoxyphenyl-6-methyl-2-oxo-1,2-dihydro-3-pyridinecarbonitrile A solution of 600 mg (1.7 mmol) of 5-{4-[N-[2-amino-2-methylpropyl]carbamoylmethoxy]phenyl}-6-methyl-2-oxo-1,2-dihydro -3-pyridinecarbonitrile (prepared as described in Example 11) and 355 mg (1.7 mmol) of (2S)-3-(2-cyano-5-chlorophenoxy)-1,2-epoxypropane in 7 ml of methanol and 7 ml of DMSO is heated overnight at 80° C. under $N_2$. Solvent is removed under vacuum and the residue flash chromatographed on silica gel (90:10 $CHCl_3$:$CH_3OH$) to give the crude product as a white solid. After washing with ether, filtering, and drying at 80° C. under vacuum, 330 mg of the title compound is obtained as a white powder, m.p. 92°–98° C. Elemental Analysis (for $C_{29}H_{30}ClN_5O_5$)

|  | % C | % H | % N |
|---|---|---|---|
| Found: | 60.97 | 5.53 | 11.76 |
| Calculated: | 60.75 | 5.45 | 12.21 |

PHARMACEUTICAL COMPOSITION EXAMPLES

The following examples illustrate pharmaceutical compositions with a compound of the invention.

| (A) Oral Tablets (250 mg) | for 10,000 Tablets |
|---|---|
| Compound of Example 2 | 2500 g |
| Anhydrous lactose U.S.P. | 2.17 kg |
| Sta-Rx 1500 Starch | 300 g |
| Magnesium Stearate B.P. | 30 g |

The drug is sieved through a 250 μm sieve and then the 4 powders are intimately mixed in a blender and compressed between 8.5 mm diameter punches in a tabletting machine.

| (B) Oral Sustained Release Tablets (750 mg) | for 10,000 Tablets |
|---|---|
| Compound of Example 2 | 7500 g |
| Cutina HR** | 0.40 kg |
| Anhydrous lactose U.S.P. | 2.06 kg |
| Magnesium Stearate B.P. | 40 g |

**Cutina HR is a grade of microfine hydrogenated castor oil supplied by Sipon Products Limited, London.

The active ingredient, Anhydrous lactose and most of the Cutina HR are intimately mixed and then the mixture is moistened by mixing with a 10% solution of the remainder of the Cutina HR in Industrial Methylated Spirit OP 74. The moistened mass is granulated through a 1.2 mm aperture sieve and dried at 50° C. in a fluidized bed dryer. The granules are then passed through a 0.85 mm aperture sieve, blended with the magnesium stearate and compressed to a hardness of at least 10 kg (Schleuniger tester) on a tabletting machine with 12.5 mm diameter punches.

| (C) Oral Syrup | % w/v |
|---|---|
| Compound of Example 2 | 3.0 |
| Dilute hydrochloric acid B.P., | as required |
| Sorbitol Solution BPC | 60 v/v |
| flavor | as required |
| Distilled water | to 100 |

The drug is dissolved in some of the water with stirring by adding gradually hydrochloric acid until the pH has fallen to 5.0. The Sorbitol Solution flavor and the rest of the water are added and the pH re-adjusted to 5.0. The syrup is clarified by filtration through suitable cellulosic filter pads.

| (D) Oral Capsules (250 mg) | for 10,000 capsules |
|---|---|
| Compound of Example 2 | 2500 g |
| Sta-Rx 1500 Starch | 1450 g |
| Magnesium Stearate B.P. | 20 mg |

The drug is sieved through a 250 μm mesh sieve and is blended with the other powders. The powder is filled into No. 3 size hard gelatin capsules on a suitable filling machine.

What is claimed is:

1. A pyridone of the following formula (I):

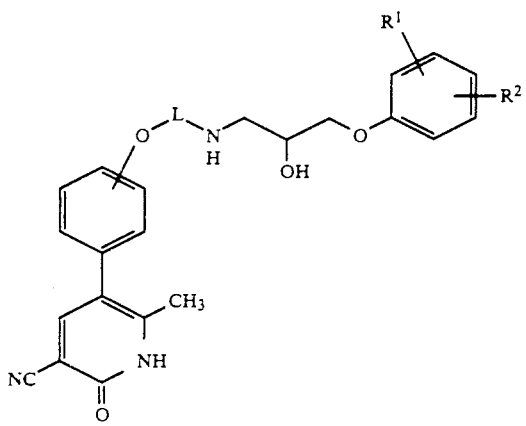

wherein:

R[1] and R[2] represent, independently, hydrogen, lower alkyloxy, morpholino, cyano, halogen, trifluoromethyl, alkyl, alkylsulfonyl, alkyloxyalkyl, cycloalkylalkyloxyalkyl, nitro, hydroxy, alkenyloxy, amino or amino substituted by one or two alkyl groups;

L represents a linking moiety of the following formula (II):

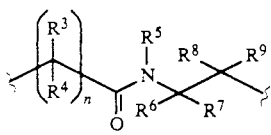

in which:

R[3]–R[9] represent, independently, hydrogen or lower alkyl;

n represents the integer 1, 2 or 3;

or a pharmaceutically acceptable acid addition salt thereof.

2. The pyridone of claim 1, wherein L is a moiety of the formula (II) and n is 1.

3. The pyridone of claim 1, wherein L is a moiety of the formula (II) and n is 1 or 3.

4. The pyridone of claim 1, wherein R[3], R[4], R[5] and R[6] are hydrogen.

5. The pyridone of claim 1, wherein R[8] and R[9] are methyl.

6. The pyridone of claim 1, wherein R[1] is hydrogen.

7. The pyridone of claim 1, wherein R[2] is cyano, chlorine or methyl.

8. The pyridone of claim 1, wherein R[1] is hydrogen and R[2] is other than hydrogen and is substituted at the 2-position of the phenyl ring.

9. The pyridone of claim 1, wherein said pyridone has the S configuration at the 2-hydroxy position shown in formula (I).

10. The pyridone of claim 1, wherein said pyridone is:
5-{4-[N-[2-(3-phenoxy-2-hydroxypropylamino)ethyl]-carbamoylmethoxy]phenyl}-6-methyl -2-oxo-1,2-dihydro-3-pyridinecarbonitrile;
5-{4-[N-[2-(3-phenoxy-2-hydroxypropylamino)ethyl]-carbamoylpropyloxy]phenyl}-6-methyl -2-oxo-1,2-dihydro-3-pyridinecarbonitrile;
5-{3-[N-[2-(3-phenoxy-2-hydroxypropylamino)ethyl]-carbamoylmethoxy]phenyl}-6-methyl -2-oxo-1,2-dihydro-3-pyridinecarbonitrile;
5-{3-[N-[2-(3-phenoxy-2-hydroxypropylamino)ethyl]-carbamoylpropyloxy]phenyl}-6-methyl -2-oxo-1,2-dihydro-3-pyridinecarbonitrile;
5-{2-[N-[2-(3-phenoxy-2-hydroxypropylamino)ethyl]-carbamoylmethoxy]phenyl}-6-methyl -2-oxo-1,2-dihydro-3-pyridinecarbonitrile;
5-{2-[N-[2-(3-phenoxy-2-hydroxypropylamino)ethyl]-carbamoylpropyloxy]phenyl]}-6-methyl -2-oxo-1,2-dihydro-3-pyridinecarbonitrile; or
5-{4-[N-[2-[3-(2-cyanophenoxy)-2S-hydroxypropylamino]-2-methylpropyl]carbamoylpropyloxy]-phenyl-6-methyl-2-oxo-1,2-dihydro-3-pyridinecarbonitrile.

11. The pyridone of claim 1, wherein said pyridone is:
5-{4-{N-[2-[3-(2'-chlorophenoxy)-2S-hydroxypropylamino]-2-methylpropyl]carbamoylpropyloxy]-phenyl-6-methyl-2-oxo-1,2-dihydro-3-pyridinecarbonitrile;
5-{4-[N-[2-[3-(2-cyanophenoxy)-2S-hydroxypropylamino]-2-methylpropyl]carbamoylmethoxy]-phenyl-6-methyl-2-oxo-1,2-dihydro-3-pyridinecarbonitrile;
5-{4-[N-[2-[3-(2-chlorophenoxy)-2S-hydroxypropylamino]-2-methylpropyl]carbamoylmethoxyphenyl-6-methyl-2-oxo-1,2-dihydro-3-pyridinecarbonitrile; or
5-{4-[N-[2-[3-(2-cyano-5-chlorophenoxy)-2S-hydroxypropylamino]-2-methylpropyl]carbamoylmethoxyphenyl-6-methyl-2-oxo-1,2-dihydro-3-pyridinecarbonitrile.

12. A pharmaceutical composition comprising a pyridone of claim 1 and a pharmaceutically acceptable diluent or carrier.

13. A method for the treatment of congestive heart failure which comprises administering to a patient in need of such the pharmaceutical composition of claim 12.

* * * * *